United States Patent [19]

Schindler et al.

[11] 4,197,852
[45] Apr. 15, 1980

[54] CATHETER ELECTRODE FOR ELECTROCHEMICAL ANALYSIS

[75] Inventors: Johannes G. Schindler, Marburg an der Lahn; Wilfried Schäl, Bad Homburg von der Hohe, both of Fed. Rep. of Germany

[73] Assignee: Dr. E. Fresenius Chemisch Pharmazeutische Industrie KG Apparatebau KG, Bad Homburg, Fed. Rep. of Germany

[21] Appl. No.: 912,884

[22] Filed: Jun. 5, 1978

[30] Foreign Application Priority Data

Jun. 11, 1977 [DE] Fed. Rep. of Germany ....... 2726450

[51] Int. Cl.² ............................................. G01N 27/46
[52] U.S. Cl. .................................. 128/635; 204/195 P
[58] Field of Search ............................. 204/1 P, 195 P; 128/635

[56] References Cited

U.S. PATENT DOCUMENTS

| | | | |
|---|---|---|---|
| 3,098,813 | 7/1963 | Beebe | 204/195 P |
| 3,211,638 | 10/1965 | Halvorsen | 204/195 P |
| 3,259,124 | 7/1966 | Hillier et al. | 204/195 P |
| 3,380,905 | 4/1968 | Clark | 204/195 P |
| 3,505,195 | 4/1970 | Nielsen et al. | 204/195 P |
| 3,528,403 | 9/1970 | Imredy et al. | 204/195 P |
| 3,718,563 | 2/1973 | Krull et al. | 204/195 P |
| 3,718,567 | 2/1973 | Haddad et al. | 204/195 P |
| 3,758,398 | 9/1973 | Doniguian | 204/195 P |
| 3,835,014 | 9/1974 | Huffhines | 204/195 P |
| 3,999,284 | 12/1976 | Bicher | 204/195 P |

OTHER PUBLICATIONS

N. A. Baker, Medical & Biological Engineering, vol. 13, No. 3, pp. 443-449, May 1975.
K. Ring et al., Arch. Mikrobiol., 65, pp. 48-60, (1969).

Primary Examiner—G. L. Kaplan
Attorney, Agent, or Firm—Omri M. Behr

[57] ABSTRACT

The electrical sensor of the present invention for electrochemical analysis comprises a sheath and at one end thereof a semi-permeable membrane which is impermeable for macromolecular materials and bacteria, and further is comprising a measuring probe insertible to said sheath.

The sheath is constructed in the form of a pericatheter and the measuring probe comprises a completely self-contained sensor, capable of operating independently of the said sheath, the membrane of said sensor being in direct contact with the membrane of said pericatheter.

2 Claims, 2 Drawing Figures

CATHETER ELECTRODE FOR ELECTROCHEMICAL ANALYSIS

BACKGROUND OF THE INVENTION

The invention is directed to sensors for electrochemical analysis, in particular for measurements which are carried out within a living body.

Ion selective, gas sensitive and enzymic sensing electrodes have in recent times attained considerable importance and recognition for several types of electrochemical measurements, in particular in the physiology and pathophysiology. It has been found desirable in many cases that such measurements take place in a precisely predeterminable location in the living body. In order to succeed in solving this problem the sensing electrodes must be constructed in the form of a catheter.

In many cases it is desirable to measure several different parameters, for example different types of ions, different types of gases or combinations thereof. The introduction of numerous catheters at the same time is however hardly possible in most cases. Even if it were possible to insert several catheters at short time intervals in the patient such a procedure would cause considerable strain and discomfort to the patient.

Multi-measuring probes have been developed which make it possible to carry out simultaneous measurement of several parameters. Unfortunately the introduction of such multi-probes having multielectrodes into a catheter of rather small diameter creates considerable practical difficulties. In addition to this such catheters with multielectrodes are extremely expensive; in particular in intensive care situations several groups of patients must be provided with such catheter-electrodes and these catheter-electrodes must be watched and serviced simultaneously.

In the continuous measurement of dissolved oxygen in fermentation cultures it has been suggested that the well-known platinum electrode (in accordance with Clark) be divided into two structural parts, namely a portion having a cathode and an anode on one hand and on the other hand an outer body for supporting the membrane necessary for the stabilization of the oxygen diffusion (K. Ring, S. Schlecht, W. Eschweiler and J. Kutscher: An Electrode for the Continuous Measurement of Dissolved Oxygen (pO2) in Fermentation Cultures (title translation), Archiv fur Mikrobiologie, vol. 65, 1969, p.48–60).

In this procedure there is provided a sheath which serves as the outer body, which can be sterilized with the fermentation vessel. The measuring probe comprising the cathode and the anode is introduced into the sheath. The connection between the cathode and the anode is obtained by introducing an electrolyte into the outer body, that is to say the sheath. The membrane operates as a stabilizer in the continuous measurement process and further separates the measuring portion of the measuring arrangement from the culture itself, so that a contamination of the measuring probe is avoided. Without the membrane it would not be possible to obtain a stable reading and also not be possible to plot the polarographic measuring curve. In order to obtain proper spacing the platinum electrode of the probe is covered with a further membrane which, in the operating position, is in direct contact with the outer membrane. Thus the diffusion path of the oxygen is stabilized and held constant, so that the measurement thereof is less influenced by turbulence in the test solution. The combination of measuring probe and sheath therefore provides a selfcontained complete item which may be utilized for the measurement of the partial pressure of oxygen but is not suitable for any other purpose.

SUMMARY OF THE INVENTION

The present invention provides the facility for repeated measurements of the same or different parameters in a living body, including a culture, without a need to change the catheter for every measurement. This is achieved by constructing a sheath similar to that described herein above in the form of a pericatheter, and providing a measuring probe introduceable thereinto, the said probe being a complete and selfcontained sensor. In this manner it becomes possible to measure not only the partial pressure of oxygen, but also other parameters one after another as desired, so that the appropriate measuring probe can be introduced into the pericatheter which is already situated in the body or system to be measured. By the use of a multi-functional probe it is possible to obtain the simultaneous provision of measurement data by several patients one after the other.

Two basis types of probes are of interest for use in pericatheters, although the invention is not limited thereto. For use with gas sensitive measuring probes it is desirable to utilize a gas-permeable but ion-impermeable membrane. It is known, for example, that polytetrafluoroethylene and polyethylene foils exibit this property. The measuring probe is, suitably, provided with foils of this type and the probe foil and the sheath foil lie in direct contact with each other. Thus the gas molecules may diffuse through both foils and reach the measuring electrode. Under steady diffusion conditions between a gas-containing substrate in which the pericatheter is located and the upper surface of the electrode, the concentration of the gas molecules in the substrate may be determined by measuring the current strength under the appropriate outer potential, and thus the partial pressure of the gas may be calculated.

Where the use of ion selective measuring electrodes are indicated, the membrane of the pericatheter must be permeable to the appropriate ions. It has been found that membranes which are permeable to low molecular ions which are used as steriliziable dialysing membranes may be employed for this purpose. Such membranes are well known in the art, for example, there may be utilized materials such as polycarbonate, polysulfone or derivates of cellulose.

The contact, suitably an electroconductive contact, between the inner portion of the membrane, and the electrode of the membrane of the measuring probe can be achieved through a liquid or gaseous pathway or a combination of the two by means well-known in the art. It has been found that a dialysis membrane may also be used for electrochemical-enzymic measurements, where the measuring probe contains a gas sensitive measuring electrode which is in series with an enzyme or multi-enzyme system. This enzyme system converts its substrate under generation of gases which may be measured by the gas sensitive electrode of the measuring probe.

Similarily the enzyme-multienzyme-system may also be connected in series to the pericatheter, that is to say in a direct contact with the membrane itself. In these circumstances the membrane of the pericatheter is, suitably, a polytetra-fluorethylene foil, through which the gas generated by the enzyme system can diffuse, so that it may be measured by the gas sensitive electrode of the measuring probe.

Where this arrangement is utilized no useful data may be obtained without the presence of an enzymic system.

The foregoing combinations of basic types of pericatheters and measuring probes should be considered exemplary only and not limiting. All types exemplified herein are illustrated in the drawings.

DETAILED DESCRIPTION OF THE DRAWINGS

Figure 1:
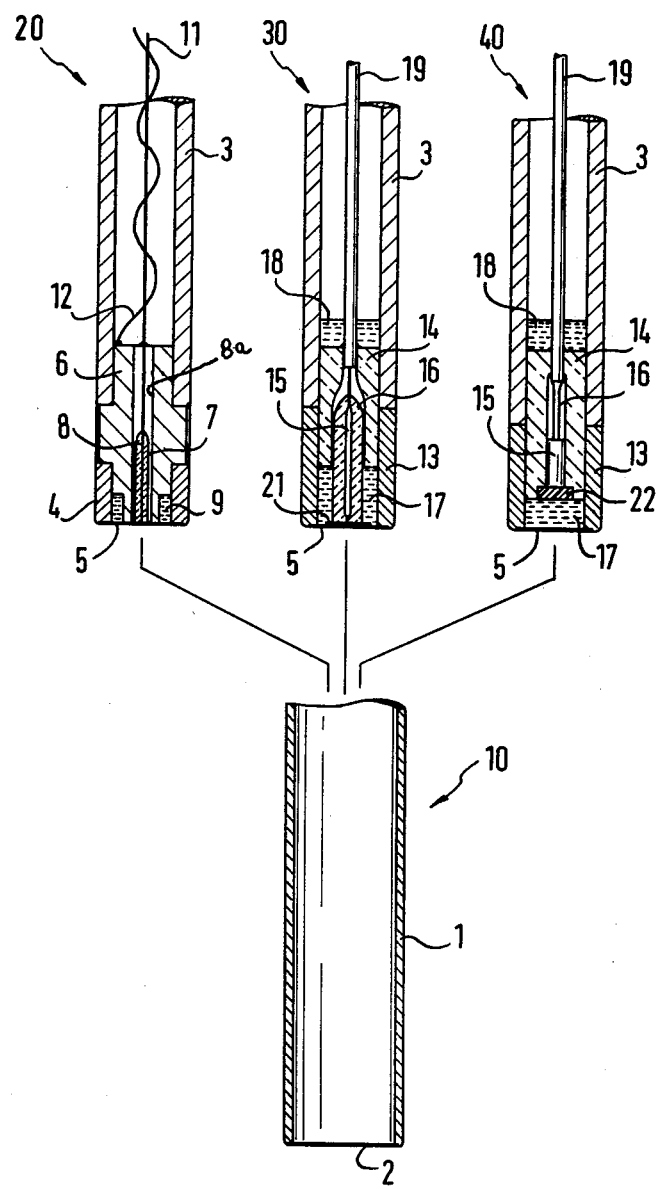
FIG. 1 is a schematic representation of several catheter electrode systems for gas sensitive measuring probes.

In the lower portion of FIG. 1 a first embodiment of the end of the pericatheter is illustrated in a cross sectional elevational view. The pericatheter 10 comprises a sterilizable hose 1 which is closed at one end thereof by membrane 2. The membrane in this embodiment is a polytetrafluorethylene foil, whose outer edge is, suitably, welded to the end of hose 1. In view of the gas permeability of membrane 2, different sorts of gas sensitive measuring probes may be inserted. Certain exemplifications of such probes are illustrated in the upper portion of FIG. 1.

The measuring probe 20 is utilized for the polarographic determination of oxygen partial pressure. It comprises a main body 3, having a removeable cap means 4. The cap means is provided with a retaining means, suitably a threaded or pressure activated retaining means. The cap 4 is further provided with a membrane 5, suitably a polytetrafluorethylene foil membrane, which upon insertion of the measuring probe 20 into the pericatheter, comes into close contact with the membrane 2 of pericatheter 10.

Into the volume surrounded by sheath 3 and cap 4 there is inserted a reference electrode 6, suitably a silver electrode. An axial channel 8a is provided in said electrode 6, through which passes a platinum wire 8 suitably surrounded by a glass coating 7. Suitably the said wire has a diameter of the order of 15 μm. At the lower end of the reference electrode there is provided an internal solution 9, suitably an aqueous solution of potassium-chloride which serves as an electrolyte, so that the currents may pass between measuring electrode 8 and the reference electrode 6. The outer potential is applied to the measuring electrode via a polytetrafluorethylene insulated copper wire 11 and to the reference electrode via a varnished copper wire 12.

The above described measuring probe is entirely selfcontained. When it is introduced into a pericatheter 10, the polytetrafluorethylene foils 2 and 5 which, suitably, have a thickness of approximately 12 μm are placed into mutual contact, so that the oxygen dissolved in the blood stream or the like may diffuse through the foils to the measuring electrode 8.

If a negative potential is applied to this electrode 8, the molecules of oxygen arriving at the outer surface of this electrode, are reduced. From the strength of this reduction current the concentration of the oxygen molecules may be determined and thus the partial pressure thereof in the blood or the like in the general environment of membrane 2 may also be determined.

The measuring probe 30 is constructed in a similar manner to measuring probe 20 and serves as a gas-measuring device by means of a glass-coated electrode. Similarly in this case there is provided a surrounding sheath 3 upon which is set a cap 13. Inside cap 13 there is provided a stopper 14 made of an isolating material, suitably polytetrafluorethylene or acrylic glass. This stopper serves as a retainer for platinum electrode 15 which is entirely encoated with glass. This glass-coating 16 is provided to have ion selective properties. The stopper 14 further serves to substantially separate the internal solution 17 surrounding the glass-coating 16 from the reference solution 18. The stopper 14 is, however, provided with a micro-channel (not shown) which provides electronic contact between solutions 17 and 18. The reference solution 18 further contains a reference electrode which is not illustrated in the drawing. The contact to the platinum electrode 15 is designated 19. In order to provide a constant diffusion path between the polytetrafluorethylene foil 5 and the head portion of the glass-coating 16, there is introduced a thin foil 21 suitably of cellophane, nylon, tissue paper or the like.

In operation of this device, the gas molecules diffusing through membranes 2 and 5 bring about a fluctuation of the pH in the inner solution 17, whereby the electrochemical potential of the platinum electrode 15 is altered. This potential change is also a means of measuring the concentration of the appropriate gases.

A highly selective mode of gas-measurement is provided by measuring probe 40. It is essentially similarily constructed as probe 30, however there is further provided between inner solution 17 and the platinum electrode 15, a foil of synthetic material 22 which is soaked in an organic ion selective substance.

When for example it is desirable to measure the concentration of ammonia, the plastic material, prior to a measurement, is mixed with the solution of valinomycin in diphenylether or nonactinmonactin in tris-ethylhexyl-phosphate. The ammonium ions diffusing therethrough react with these substances and lead to a change of potential at the probe-electrode 16.

Figure 2:
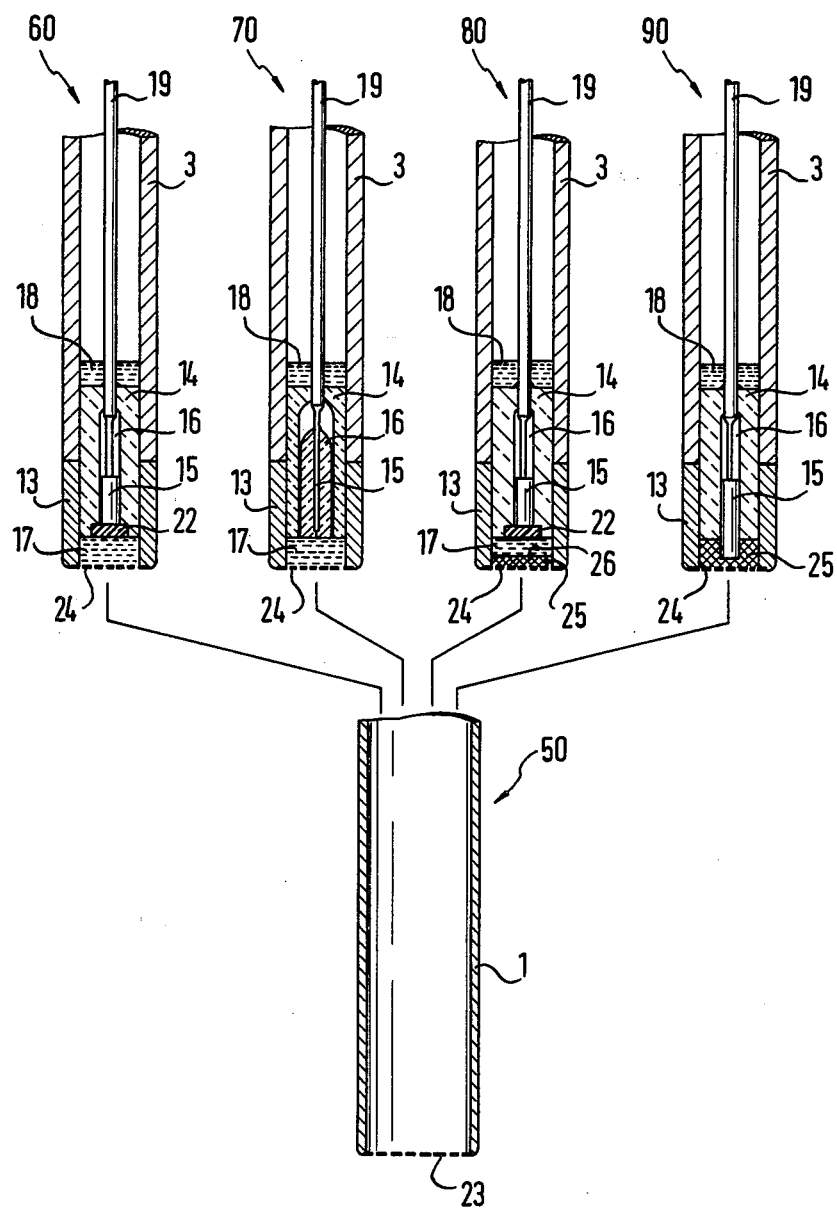
FIG. 2 is a schematic representation of examples of ion selective, gas sensitive and enzyme-activated measuring probes.

The catheter-electrode-system illustrated in FIG. 2 is designed, in particular, for ion selective measurements. The pericatheter 50 again comprises a hose-typed sheath 1, but this time the membrane 23 will permit the diffusion therethrough of low molecular weight substances. Nevertheless it must of course meet the sterilisation requirements set forth hereinabove. Such a membrane is designated a dialysis membrane. Among the substances known to the art which may be utilized therefor are cellophane, polycarbonate, polysulfone or derivates of cellulose and the like.

Some exemplifying but in no way limiting examples of measuring probes, suitable under these circumstances, are illustrated as items 60-90 in FIG. 2. These examples of course are not to be considered as limiting upon the invention.

The measuring probe 60 is similarly constructed as measuring probe 40 in FIG. 1. The sole difference therebetween exists in that in place of providing a gas-permeable membrane 5, a dialysis membrane 24 is provided at the end of cap 13. The mode of operation of the measuring electrode does not alter since the gases to be measured have a low molecular weight and therefore may pass through a polytetrafluorethylene foil as well as through a dialysis membrane.

The measuring probe 70 in FIG. 2 similarly corresponds to a substantial degree to the measuring probe 30 in FIG. 1. The principal difference is found therein that in place of a polytetrafluorethylene foil 5, a dialysis membrane 24 is provided in cap 13. Further the glass-covered electrode 15 is set further away from membrane 24 so that a larger amount of the internal solution 17 is located between said membrane 24 and said electrode 15. This causes the electrode to be, to all intents, no longer gas sensitive but ion selective. The type of the ions indicated (i.e. measured) depends upon the properties of the internal solution 17 and the selectivity of the glass-coating.

The measuring probes 80 and 90 illustrate two examples for electrochemical-enzymatic measuring arrangements.

The measuring probe 80 serves as a pre-membranic conversion system of a gas sensitive electrode placed in series with an enzyme or multi-enzyme system. The electrode is essentially identical with the measuring probe 60, however a mutli-enzyme system is placed in series with the ion selective polymeric foil 22 and the inner solution 17 so that the inner solution 17 is separated from the enzyme or multi-enzyme system by a gas-permeable foil 26. When the substance to be measured (for example glucose) has diffused through membranes 23 and 24 into the enzyme or multi-enzyme system 25, this system converts its substrate under the generation of gases, which pass through the polytetrafluorethylene foil 26 to the gas sensitive measuring electrode 16 causing potential changes to occur.

The measuring probe 90 serves as a post-membranic converter through electrolytic oxidation of the reduced acceptor. The enzyme or multi-enzyme system 50 stands in direct contact with the platinum electrode 15. The strength of the measuring current at a predetermined potential applied to the measuring electrode is a measure of the degree of conversion of the enzymic substrate and thus provides a measure for the low molecular weight substance causing the conversion.

We claim:
1. An electrochemical analysis sensor comprising:
   (a) a sheath constructed as a pericatheter being closed at one end thereof by a semi-permeable membrane being an integral part thereof, said membrane being permeable to certain predetermined substances, but impervious to macromolecules and bacteria; and
   (b) a replaceable measuring probe having a membrane at one end thereof, disposed in said sheath, said measuring probe being a completely self-contained sensing device, said probe membrane and said sheath membrane being in intimate contact and free of electrolyte therebetween.
2. A sensor wherein said pericatheter sheath and said measuring probe are a flexible tube.

* * * * *